(12) United States Patent
Killich

(10) Patent No.: US 9,304,079 B2
(45) Date of Patent: Apr. 5, 2016

(54) GAS ANALYSER

(71) Applicant: METTLER-TOLEDO AG, Greifensee (CH)

(72) Inventor: Frank Killich, Bad-Zwesten (DE)

(73) Assignee: METTLER-TOLEDO GMBH, Greifensee (CH)

(*) Notice: Subject to any disclaimer, the term of this patent is extended or adjusted under 35 U.S.C. 154(b) by 0 days.

(21) Appl. No.: 14/302,997

(22) Filed: Jun. 12, 2014

(65) Prior Publication Data

US 2014/0291526 A1   Oct. 2, 2014

Related U.S. Application Data

(63) Continuation of application No. PCT/EP2012/075352, filed on Dec. 13, 2012.

(30) Foreign Application Priority Data

Dec. 15, 2011  (EP) .................................. 11193681

(51) Int. Cl.
*G01N 21/3504*  (2014.01)
*G01N 21/39*  (2006.01)
(Continued)

(52) U.S. Cl.
CPC ............ *G01N 21/3504* (2013.01); *G01N 21/39* (2013.01); *G01N 21/8507* (2013.01);
(Continued)

(58) Field of Classification Search
CPC ............. G01N 21/35; G02B 5/04; G02B 5/02
USPC ........................................................ 250/343
See application file for complete search history.

(56) References Cited

U.S. PATENT DOCUMENTS 210,956 A    12/1878  Osgood
2,557,096 A *  6/1951  Golay .................... 250/338.1
(Continued)

FOREIGN PATENT DOCUMENTS

CN    101008604 A   8/2007
CN    201016927 Y   2/2008
(Continued)

OTHER PUBLICATIONS

International Preliminary Report on Patentability (Form PCT/IB/373) and Written Opinion of the International Searching Authority (Form PCT/ISA/237) issued on Jun. 17, 2014, by the international Bureau of WIPO in corresponding International Application No. PCT/EP2012/075352. (8 pages).
(Continued)

*Primary Examiner* — David Porta
*Assistant Examiner* — Faye Boosalis
(74) *Attorney, Agent, or Firm* — Buchanan Ingersoll & Rooney PC

(57) ABSTRACT

A gas analyzer for the absorption-spectroscopic in-situ determination of at least one chemical and/or physical parameter of a gaseous measurement medium, wherein the gas analyzer includes a first housing; at least one laser as a radiation source, which laser is arranged in the first housing; at least one first process window for coupling the radiation emitted by the laser into a measurement medium; and at least one detector by which, following interaction with the measurement medium, the radiation is detected. The first process window can be configured as an afocal meniscus lens having a convex surface and a concave surface.

20 Claims, 3 Drawing Sheets

(51) Int. Cl.
*G01N 21/03* (2006.01)
*G01N 21/15* (2006.01)
*G01N 21/85* (2006.01)

(52) U.S. Cl.
CPC .. *G01N2021/0392* (2013.01); *G01N 2021/151* (2013.01); *G01N 2021/399* (2013.01); *G01N 2021/8514* (2013.01)

(56) References Cited

U.S. PATENT DOCUMENTS

| | | | |
|---|---|---|---|
| 3,515,461 A * | 6/1970 | Rayces | G02B 17/0808 359/731 |
| 3,805,074 A | 4/1974 | McCormack | |
| 4,549,080 A | 10/1985 | Baskins et al. | |
| 5,331,409 A | 7/1994 | Thurtell et al. | |
| 5,781,306 A | 7/1998 | Hartig et al. | |
| 5,877,862 A | 3/1999 | Nelson et al. | |
| 5,963,336 A | 10/1999 | McAndrew et al. | |
| 6,064,488 A | 5/2000 | Brand et al. | |
| 6,115,181 A * | 9/2000 | Kelly | 359/618 |
| 6,154,284 A | 11/2000 | McAndrew et al. | |
| 6,493,086 B1 | 12/2002 | McAndrew et al. | |
| 6,841,778 B1 | 1/2005 | Shifflett et al. | |
| 7,817,355 B2 * | 10/2010 | Yamasaki | G02B 5/1895 359/744 |
| 2003/0002547 A1 | 1/2003 | Lee | |
| 2003/0063284 A1 | 4/2003 | McAndrew et al. | |
| 2009/0141273 A1 | 6/2009 | Poulter et al. | |
| 2011/0140008 A1 * | 6/2011 | Bergstedt et al. | 250/504 R |

FOREIGN PATENT DOCUMENTS

| | | |
|---|---|---|
| DE | 44 43 016 A1 | 6/1996 |
| DE | 20 2008 013 557 U1 | 3/2009 |
| EP | 0 068 037 A1 | 1/1983 |
| EP | 0 068 037 B1 | 1/1985 |
| EP | 2 065 738 A1 | 6/2009 |
| GB | 1 303 412 A | 1/1973 |

OTHER PUBLICATIONS

International Search Report (PCT/ISA/210) mailed on Jan. 22, 2013, by the European Patent Office as the International Searching Authority for International Application No. PCT/EP2012/075352.
European Search Report mailed on May 9, 2012 for Application No. 11193681.1 (6 pages).
European Search Report mailed on Sep. 4, 2012 for Application No. 11193681.1 (14 pages).

* cited by examiner

GAS ANALYSER

RELATED APPLICATIONS

This application claims priority as a continuation application under 35 U.S.C. §120 to PCT/EP2012/075352, which was filed as an International Application on Dec. 13, 2012 designating the U.S., and which claims priority to European Application 11193681.1 filed in Europe on Dec. 15, 2011. The entire contents of these applications are hereby incorporated by reference in their entireties.

FIELD

The present disclosure relates to a gas analyser with a first process window for the absorption-spectroscopic in-situ determination of at least one chemical and/or physical parameter of a gaseous measurement medium.

BACKGROUND INFORMATION

Laser absorption spectroscopy and in particular diode-laser absorption spectroscopy with the use of a tunable laser, also referred to as TDLAS (tunable diode laser absorption spectroscopy), is particularly well suited to determining at least one chemical and/or physical parameter of a gaseous measurement medium.

By way of laser absorption spectroscopy it is possible to very precisely determine the concentration or the content of a gas that is present in a measurement environment or in a measurement medium. Furthermore, it is also possible to determine further parameters, for example temperature or pressure.

With TDLAS, the measurement medium is irradiated by radiation of a tunable laser. In this technique, a wavelength of the radiation is periodically modulated in a predetermined wavelength range, wherein the wavelength range passed through by the laser can include one or several absorption bands of the gas to be analysed. The wavelength range covered is determined by the laser used, and for example more precisely, by the diode laser used. A multitude of lasers and diode lasers are known. So-called DFB lasers (distributed feedback lasers) can cover wavelength ranges between approximately 700 nm and approximately 3 μm. So-called VCSEL lasers (vertical-cavity surface-emitting lasers) can cover wavelength ranges up to approximately 2.1 μm, and QCL lasers (quantum cascade lasers) can cover wavelength ranges above approximately 3.5 μm or even above approximately 4.3 μm.

Measuring can take place in a transmission arrangement, wherein measuring in transflection arrangement is also known. The radiation emitted by the laser or the diode laser is guided through the measurement medium, and following interaction with the measurement medium is detected by a suitable detector.

Gases can be detected that include at least one characteristic absorption band or absorption line in the wavelength range used. Gases that can be detected by laser absorption spectroscopy include, among others, oxygen ($O_2$), carbon dioxide ($CO_2$), carbon monoxide (CO), nitrogen oxides ($NO_x$), amines, ammonia ($NH_3$), hydrogen sulphides ($H_2S$), sulphur oxides ($SO_2$), hydrogen halide compounds such as HCl or HF, gaseous water or even mixtures thereof.

For the determination of, for example, oxygen, a laser is suitable that, for example, emits or can be modulated in the region of 760 nm, while for the determination of $NH_3$ a laser is suitable that emits or can be modulated in the region around 1500 nm, because in these regions there is in each case a strong absorption band of oxygen or $NH_3$.

In this document, the terms "measurement environment" and "measurement medium" designate the environment or the medium in which measuring takes place, or which environment or medium is analysed.

U.S. Pat. No. 5,331,409 A discloses a gas analyser with a tunable diode laser and a connected gas analyser arrangement into which the measurement medium to be analysed is introduced, and which gas analyser arrangement includes several gas measurement cells. The radiation is directed by a collimator lens to a first measurement cell that includes a beam splitter, which directs the radiation through separate focusing lenses to a further measurement cell or a reference cell. The measurement cell and the reference cell each include a detector. However, the use of these lenses can give rise to interference that impedes the detection of the absorption bands. In order to suppress this effect to the greatest extent possible, in this arrangement the measurement cells can be designed to be particularly long.

With the use of a gas analyser in a process environment, such as in a container, the laser radiation can be coupled through a process window into the measurement medium or into the measurement environment. The process window can be a lens, as disclosed in U.S. Pat. No. 5,331,409 A. Furthermore, gas analysers are known that include wedge-shaped windows or normal windows as process windows. The wedge-shaped windows are frequently installed so as to be slightly oblique to the optical axis. Normal windows are predominantly installed below the Brewster angle; in other words also so as to be oblique to the optical axis. Depending on the alignment of the laser polarisation, installation of the process window below the Brewster angle can in itself result in signal loss, which even by the most precise adjustment possible cannot always be completely suppressed. Furthermore, with these solutions, frequently a pair of windows are installed in order to adequately correct the optical beam path, and furthermore, the process windows, for example, are coated with an anti-reflection coating in order to suppress interference effects that would otherwise occur. Interference effects can have a negative influence on the measuring results, and furthermore can result in temperature-dependent drift. In addition, because of the adjustments, precise installation of such windows can be time-consuming, and the manufacture of high-precision wedge-shaped windows can be expensive.

With the use of gas analysers in process facilities or measuring environments, above all in harsh environmental conditions, coated optical elements can, in certain circumstances, result in the coating being attacked and damaged or destroyed, which in turn results in a loss of measuring accuracy. In this context the term "harsh environmental conditions" refers to measuring environments with, for example, rather high or low temperatures, rather high or low pressures, and/or measuring environments where aggressive chemicals are used. In particular in the use in process facilities or in atmospheric research it is, furthermore, very difficult to ensure adequate adjustment of the process windows during the entire measurement cycle and/or during the service life of the gas analyser, because re-adjustments can only be made after deinstallation of the gas analyser.

Absorption-spectroscopic gas analysers can, for example, be used for in-situ monitoring of gas concentrations, in particular of oxygen, in potentially explosive processes or processes facilities, for example in oil refineries or during combustion processes. Atmospheric research is another field of application.

For controlling and/or analysing such processes and measuring environments the gas analysers used should furnish measurement values at a high level of reproducibility with great reliability and with as little maintenance as possible.

SUMMARY

A gas analyser is disclosed for absorption-spectroscopic in-situ determination of at least one chemical and/or physical parameter of a gaseous measurement medium, wherein the gas analyser includes a first housing, at least one laser as a radiation source, which laser is arranged in the first housing, at least one first process window for coupling radiation emitted by the laser into a measurement medium and at least one detector configured to detect radiation following interaction with the measurement medium wherein the first process window is configured as an afocal meniscus lens having a convex surface and a concave surface.

BRIEF DESCRIPTION OF THE DRAWINGS

Various exemplary embodiments of a gas analyser disclosed herein are described in more detail below with reference to the following figures, wherein identical elements have the same reference characters. The following are shown in the figures.

DETAILED DESCRIPTION

Figure 1:
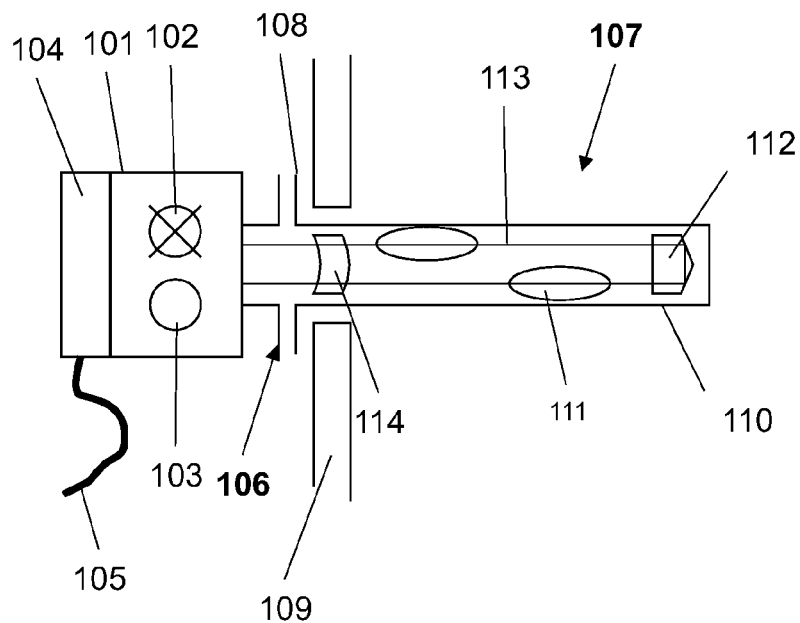
FIG. 1 shows a first exemplary embodiment of a gas analyser as disclosed herein with a first process window and a gas probe and a connected control and/or regulation unit.

An absorption-spectroscopic gas analyser with a process window for in-situ determination is disclosed, which gas analyser is particularly robust and can be used even under harsh process conditions to the greatest extent possible without any loss of measuring accuracy and reproducibility.

A gas analyser is disclosed for absorption-spectroscopic in-situ determination of at least one chemical and/or physical parameter of a gaseous measurement medium. The gas analyser can include a first housing, at least one laser as a radiation source, at least one first process window for coupling the radiation emitted by the laser into the gaseous measurement medium, and at least one detector by which, following interaction with the measurement medium, the radiation is detected. According to an exemplary embodiment, the first process window can be designed as an afocal meniscus lens that includes a convex surface and a concave surface.

The use of an afocal meniscus lens can be particularly advantageous because, due to the lack of imaging characteristics of this afocal meniscus lens, there is no need for particular alignment or adjustment of the afocal meniscus lens relative to the measurement beam, because an afocal meniscus lens has no imaging characteristics.

Meniscus lenses can be designed to be either focal, in other words imaging (i.e., as dispersing lenses and/or as converging lenses), or afocal, in other words non-imaging. In contrast to a focal meniscus lens with a finite focal length, an afocal meniscus lens has an essentially infinite focal length.

If a focal meniscus lens is used as a first process window, its geometry, such as its radii of curvature, its refractive index and its thickness at the centre of the lens, should be calculated individually for each gas analyser, and should thus be attuned as precisely as possible to the length of the measuring path and/or of further components used, for example the laser, the detector, and/or the optical reflector element. In order to ensure that reproducible measurement results are obtained, with the use of focal meniscus lenses as a first and/or second process window/s, the measuring path should have an essentially fixed length. Furthermore, because of the imaging characteristics of a focal meniscus lens as a process window, its arrangement relative to the alignment of its concave and convex surface is essentially predetermined.

According to exemplary embodiments disclosed herein, the first process window of the gas analyser is designed as an afocal meniscus lens. The use of an afocal meniscus lens as a first process window can be advantageous because the lens can be used irrespective of the length of the measuring path, which can ensure a high level of insensitivity in terms of adjustment, thus rendering the gas analyser very robust. Moreover, because of its optical characteristics, an afocal meniscus lens makes it possible to couple the laser radiation into and/or out of the measurement medium or the measurement environment in such a manner that the formation of undesired interference on the detector is prevented to the greatest extent possible.

The use of afocal meniscus lenses as process windows can be associated with a further advantage in that afocal meniscus lenses can be arranged like planar panels in any desired orientation in the gas analyser. An afocal meniscus lens can be aligned so that its concave or convex surface faces the measurement medium, without this altering the optical characteristics of the gas analyser.

Because of the optical characteristics of the afocal meniscus lens, a gas analyser can, furthermore, be implemented in a design having a non-coated process window that, for example, has no anti-reflection coating. This can be advantageous, for example, in the use of gas analysers in process facilities for in-situ determination, because in this manner any optical errors and interference as a result of the process window can be prevented to the greatest extent possible. Long-term measurement stability and reproducibility of the measurement results can be ensured and the limit of detection can be improved. A first process window designed as an afocal meniscus lens can, furthermore, be used in gas analysers as disclosed herein with various known lasers or diode lasers that emit, or are tunable to, radiation of a fixed wavelength, provided the first process window is optically translucent to the radiation used.

Materials suitable for use as the process window are, for example, borosilicate glass, quartz, quartz glass, sapphire, diamond, zinc selenide or germanium. Of course, a process window according to the disclosure can also be manufactured from some other material known in the context of optical lenses, for example from an optical glass.

Depending on the wavelength range of the laser used, various detectors known in laser absorption spectroscopy can be used as detectors, for example photodiodes, photomultipliers, photocells, InGaAs-detectors or pyroelectric detectors, wherein other known radiation detectors can also be used.

An absorption-spectroscopic gas analyser as disclosed herein can, for example, be used for the analysis of a gaseous measurement medium in any desired measurement environment. In the case of its use in a process facility, in order to determine a parameter the gas analyser is for example inserted in a container, wherein in this context the term "container" refers to various components of a process facility, in particular, for example, reaction vessels or all kinds of inlet lines or outlet lines in which absorption-spectroscopic analyses can be carried out. Furthermore, this also includes other containers or vessels in which gaseous measurement media, gases or gas mixtures can be stored, transported or used.

In one exemplary embodiment the gas analyser can, furthermore, include an optical reflector element that reflects the radiation coupled into the measurement medium through the first process window back to the first process window so that the radiation can be coupled out of the measurement medium.

The optical reflector element can, for example, include at least one of the following optical elements: one component of cat's eyes optics, a triple prism, a triple mirror, a planar mirror and/or an imaging mirror.

In a further exemplary embodiment of the gas analyser the detector and the laser can be arranged in the first housing. In this arrangement the first process window is used for coupling the radiation emitted by the laser to the measurement medium and, following interaction with the measurement medium, also for coupling the radiation from the measurement medium.

In a further exemplary embodiment the gas analyser can include a second housing and a second process window, wherein the detector or the reflector element is arranged in the second housing.

Between the first process window and the reflector element or the second process window a measuring path forms during operation, which measuring path is used for the absorption-spectroscopic detection of at least one chemical and/or physical parameter. With the use of a reflector element the radiation emitted by the laser passes twice along the measuring path on the way from the laser to the detector.

In a further exemplary embodiment the optical reflector element can be arranged in the second housing so that radiation coupled through the first process window into the measurement medium is first decoupled, through the second process window, from the measurement medium and is directed to the optical reflector element. The radiation is reflected by the optical reflector element and is directed, through the first and second process windows and the measurement medium, back to the detector, which in this arrangement is arranged in the first housing. As a result of the double transmission of the radiation through the measurement medium the limit of detection of the absorption measuring process can be increased because according to the Lambert-Beer law the length of the measuring path is directly proportional to the absorption intensity.

The arrangement of the laser, detector and/or reflector element in two housings is above all suitable for use in a so-called cross-stack arrangement or in an open-path arrangement. In a cross-stack arrangement the measurement medium is in a closed or open container that is penetrated by radiation, for example, in a pipeline. An open-path arrangement is above all used for very long measuring paths, for example in atmospheric research or in environmental research, in particular for air analysis. In a cross-stack arrangement or in an open-path arrangement it is possible for the laser to be arranged in the first housing and the detector in the second housing, or for the laser and the detector to be arranged in the first housing and for the reflector element to be arranged in the second housing.

The second process window can also be designed for example as an afocal meniscus lens that includes a convex and a concave surface. The use of two meniscus lenses as the first and second process windows is advantageous because in this way both process windows can be used without the need for a coating. Due to the optical characteristics of afocal meniscus lenses, in a gas analyser having two process windows designed as afocal meniscus lenses the afocal meniscus lenses can be oriented identically or differently relative to the measurement medium. In either arrangement the gas analyser remains robust to geometric disruptions and is, furthermore, essentially length-independent in relation to the measuring path. Furthermore, it is also possible to use an afocal meniscus lens together with a focal meniscus lens.

The thickness of the afocal meniscus lens can be adjusted to take account of specific conditions of service. For example, it is possible, by way of the thickness of the afocal meniscus lens, to adjust the pressure resistance of the aforesaid within a certain range. The thicker the afocal meniscus lens, the higher is the pressure resistance of the process window, constructed in this manner, and of the associated gas analyser.

Suitable afocal meniscus lenses can be calculated with the use of the following exemplifying equations for calculating the lens thickness, more precisely the thickness at the centre of the lens, and for calculating the convex radius R2:

$$d = (R2 - R1) \times \left(\frac{n}{n-1}\right)$$

$$R2 = R1 + \frac{d}{a} \text{ with } a = \left(\frac{n}{n+1}\right)$$

wherein n denotes the refractive index of the lens material, d the thickness at the centre of the lens, R1 the concave radius, and R2 the convex radius. An afocal meniscus lens calculated according to these equations essentially has no imaging effect, in other words is afocal. Such an afocal meniscus lens, furthermore, is associated with little enlargement or reduction in size of the radiation passing through it, more precisely of the diameter of the beam of rays, similar to field glasses set to infinity. This can result, for example, in an advantageous change in the distance between the two measurement beams, in other words the radiation from the laser to the reflector element, and from the reflector element to the detector.

In a further exemplary embodiment the gas analyser can include a gas probe that includes an essentially cylindrical probe body with at least one process opening through which during operation the measurement medium can enter into the interior of the probe body.

The embodiment of the gas analyser with the gas probe is, for example, advantageous for taking measurements in the interior of a container because in this manner a defined measuring path can be formed in the interior of the container.

For example, the probe body can essentially include (e.g., consist of) a metallic material, for example a stainless steel, a nickel alloy, such as a nickel-molybdenum alloy, titanium, zirconium or tantalum; or a plastic material, for example, PEEK, PMMA or POM; or mixtures thereof.

The gas probe can be configured as a second housing, or it can be arranged between the first and the second housing, wherein in either case one end of the gas probe is connected to the first housing and/or to the second housing.

Furthermore, the gas probe can include at least one purge gas connection for a purge gas, as well as a purge-gas line. The use of a purge gas serves to improve the quality of the measurement results, because in this manner the gas probe can be purged or flushed with the purge gas, entirely or partly, so that deposits and/or undesirable residues of the measurement medium can be removed, and thus comparable starting conditions can be provided for each measurement.

For example, the purge-gas line is arranged in the probe in such a manner that in operation the first and/or the second process windows or window include(s) a purge-gas cushion on the side of the medium. In this manner deposits occurring on the meniscus lens can be greatly reduced, and in turn measuring accuracy can be improved.

In a further exemplary embodiment of the gas analyser the optical reflector element is attached without a seal on the end of the gas probe, which end faces away from the first housing. Furthermore, the purge-gas line can include a discharge opening in the region of the optical reflector element so that in operation purge gas flows around the optical reflector element.

The first process window can be arranged in the first housing or on the end of the gas probe, which end faces the first housing. The second process window can be arranged in the second housing or on the end of the gas probe, which end faces away from the first housing.

Furthermore, the gas analyser can include at least one connection or flange for connecting the gas analyser to a container. Depending on the embodiment, the at least one connection or flange can be arranged on the first housing, on the second housing and/or on one and/or both ends of the gas probe.

A gas analyser disclosed herein can, for example, be used for absorption-spectroscopic determination of one or several of the following chemical and/or physical parameters. These parameters include, among others, the temperature or the pressure of the measurement medium and/or the concentration of a gas, for example, oxygen, carbon dioxide, carbon monoxide, nitrogen oxides, amines, ammonia, hydrogen halides, hydrogen sulphides, sulphur oxides, water or mixtures thereof.

Furthermore, the gas analyser can include a control and/or regulation unit which at least in part is arranged in the first and/or second housing. It is also possible that the control and/or regulation unit is designed essentially as a separate device that is connected, wirelessly or in a wire-bound manner, to the gas analyser.

In terms of the laser, the gas analyser can include a tunable diode laser. For oxygen determination it is possible, for example, to use a laser or diode laser that emits or is tunable in a wavelength range of approx. 700 to approx. 800 nm, wherein the wavelength range of the laser can include at least one of the known oxygen-absorption bands.

FIG. 1 shows a highly diagrammatic view of a gas analyser according to an exemplary embodiment as disclosed herein. The gas analyser can include a first housing 101 in which a laser 102 as a radiation source and a detector 103 are arranged. In this design the first housing 101 can essentially correspond to a spectrometer, and can include a tunable diode laser as a laser 102, as is used for TDLAS and is disclosed, for example, in DE 20 2008 013 557 U1. The housing 101 is connected to a control and/or regulation unit 104 (only diagrammatically indicated) which in turn, by way of a suitable wireless connection, or as shown in the diagram a wire-bound connection 105, can be connected to a higher-level control device, for example to a process control system.

The control and/or regulation unit 104 can be connected to the housing 101 as shown in the diagram; however, it can also be arranged partly in the housing 101 and can be connected to the housing 101 wirelessly or in a wire-bound manner. The control and/or regulation unit 104 is, for example, used to transmit control commands and/or predetermined parameters to the gas analyser, to control the laser 102, and to acquire the data and/or raw data obtained by the detector 103, and to transmit said data to a suitable evaluation unit.

Figure 2:
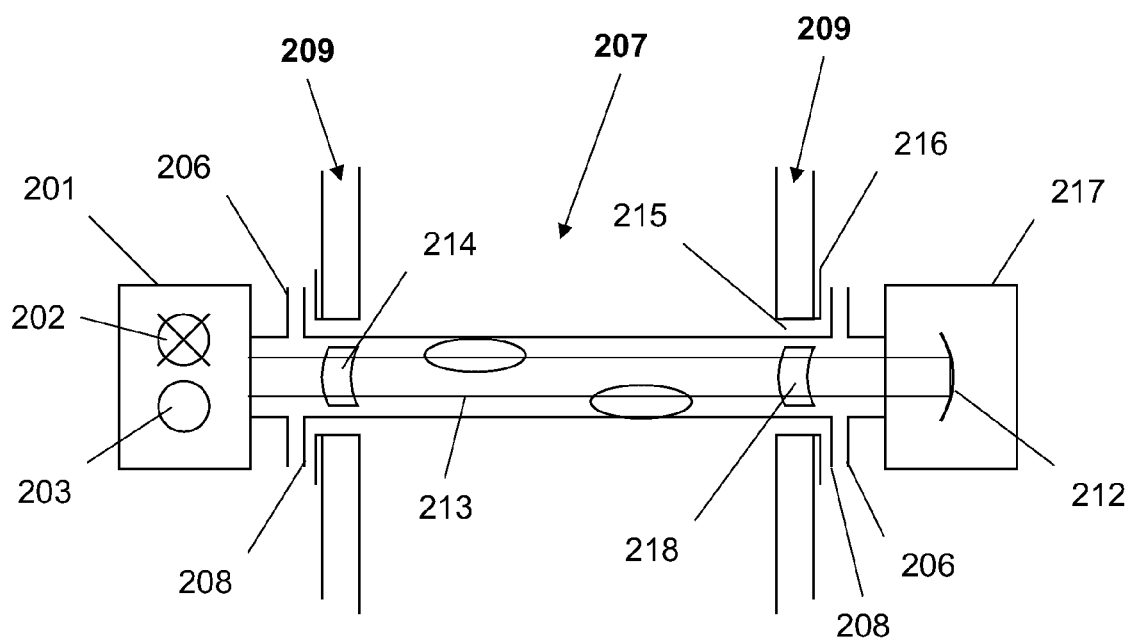
FIG. 2 shows a second exemplary embodiment of a gas analyser as disclosed herein with a first and a second process window and a gas probe that is arranged between a first and a second housing, wherein in the second housing an optical reflector element is arranged.
Figure 5:
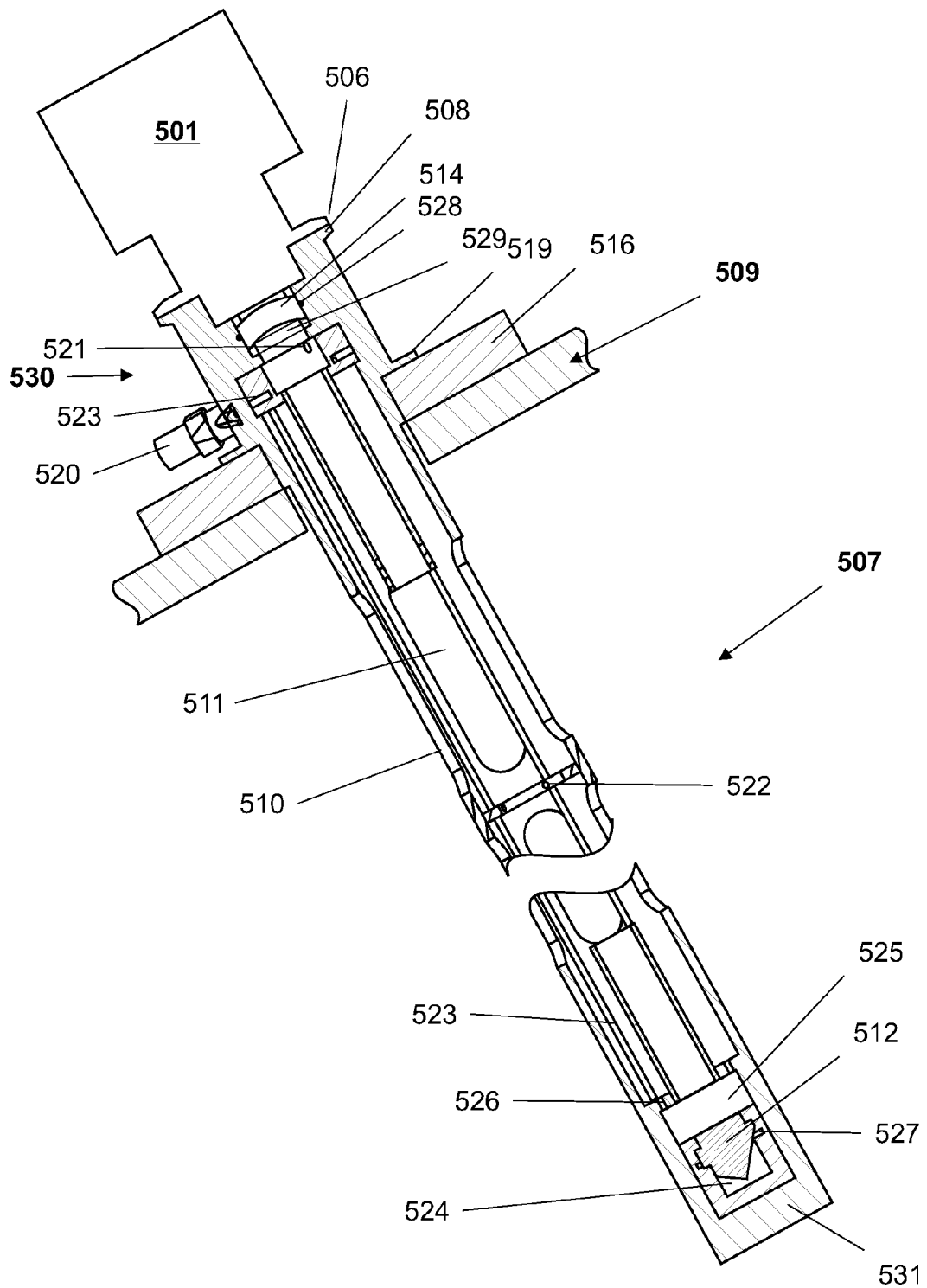
FIG. 5 shows a section drawing of a gas analyser as disclosed herein with a first process window and a gas probe, an optical reflector element and a purge-gas line.

Furthermore, the housing 101 can include a first flange 106 for connection to a counterflange 108 of a gas probe 107. The gas analyser can, as shown in the diagram, by way of the flange 106 and the counterflange 108, be connected to a container 109, the wall of which is indicated in the diagram. For example, to this effect the container 109 can include a further flange, as shown in FIG. 2. The gas analyser can also, as shown in FIG. 5, include a further flange that is suitable for connection to the container 109. In the context of process facilities various flange systems and flange types are known, which are therefore not explained in detail in this document.

The gas probe 107 can include an essentially cylindrical probe body 110 that has one or several process openings 111 by way of which a measurement medium can enter the gas probe or can flow through said gas probe. As shown in the diagram, the process openings 111 can be arranged so as to be offset or so as to be situated along a shared axis. Furthermore, it can be advantageous if a gas probe 107 includes several process openings 111 situated opposite each other so that the gaseous measurement medium can flow with as little hindrance as possible through the probe body 110.

In the end of the gas probe 107, which end is situated opposite the housing 101, there is an optical reflector element 112 that serves to reflect the radiation emitted by the laser 102, as in the optical beam path 113 that is merely indicated in the diagram, to the housing 101 and, for example, to the detector 103 arranged therein. In this manner the radiation travels twice along the measuring path in the measurement medium on the way between the laser 102 and detector 103. Apart from the triple prisms shown in the diagram, other components can also be used as an optical reflector element 112, for example at least one component of cat's eyes optics, a planar or imaging mirror or a triple mirror.

As a process window 114 an afocal meniscus lens is arranged in the gas probe 107. In FIG. 1 the convex surface of the meniscus lens faces the measurement medium. As already mentioned, an afocal meniscus lens can also be used the other way round, in other words with the convex surface facing away from the measurement medium.

The process window 114 is sealed off from the probe body 110 by means of a suitable sealing device, for example an O-ring. It can be very advantageous if the process window 114 is arranged in the gas probe 107 because in this way the gas probe 107 is closed off against the outside and no further window is used for separation between the container 109 and the environment. Furthermore, the housing 101, which essentially includes the spectrometer, can easily be deinstalled and can, for example, be adjusted and/or calibrated under controlled conditions. Furthermore, in this manner it is possible to exchange the spectrometer so that, for example, measurements in different laser wavelength ranges can be carried out in the same container or in the same measurement environment.

FIG. 2 shows a highly diagrammatic view of a second exemplary embodiment of the gas analyser as disclosed herein. As shown in the diagram, the gas analyser is installed in a pipeline or in some comparable container 209. In the wall of the container 209 there are opposing lead-throughs 215 for accommodating the gas analyser, with each of the lead-throughs 215 having a flange stub 216 on the outside.

The gas analyser can include a first housing 201, in which a laser 202 and a detector 203 are arranged, and a housing 217 that is situated opposite the first housing 201, in which an optical reflector element 212, namely a mirror in the diagram shown, is arranged. Both housings 201, 217 can include a flange 206 by means of which the respective housing can be attached to a gas probe 207 and/or to the container 209.

The gas probe 207 can include several process openings 211 as well as a first and a second process window 214, 218, respectively arranged at one end of the gas probe, in the optical beam path 213. Both process windows 214, 218 are designed as afocal meniscus lenses. The first process window 214 is placed in the optical beam path in such a manner that the concave surface of the afocal meniscus lens faces the measurement medium, and the second process window 218 is placed in such a manner that the convex surface of the afocal meniscus lens faces the measurement medium. The two process windows 214, 218 in turn close off the gas probe and thus the container 209, more precisely the lead-throughs 215, towards the outside so that one or both of the housings 201, 212 can be removed without any measurement medium emanating from the container 209 to the environment.

Figure 3:
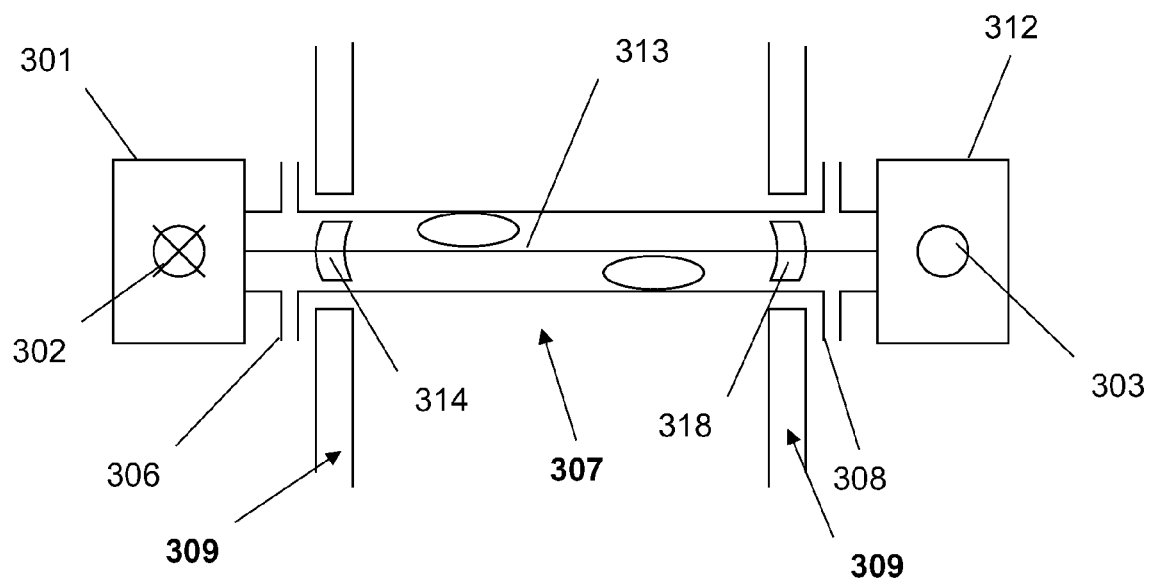
FIG. 3 shows a third exemplary embodiment of a gas analyser as disclosed herein with a first and a second process window and a gas probe that is arranged between a first and a second housing, wherein in the second housing a detector is arranged.

FIG. 3 shows a highly diagrammatic view of a third exemplary embodiment of the gas analyser. In contrast to the gas analysers shown in FIGS. 1 and 2, in this arrangement a laser 302 is arranged in a first housing 301 and a detector 303 is arranged in a second housing 312. In turn, by way of suitable flanges, the two housings 312 are connected to a gas probe 307 and/or to a container 309, for example a pipeline. The gas probe 307 essentially corresponds to that already shown in FIG. 2, wherein both the first and the second process windows 314, 318 are designed as afocal meniscus lenses whose concave surfaces in the diagram shown are aligned to the measurement medium. Because of the spatial separation of the laser 302 from the detector 303, the radiation from the laser 302 passes only once through the measurement medium, as indicated by the optical beam path 313.

Figure 4:
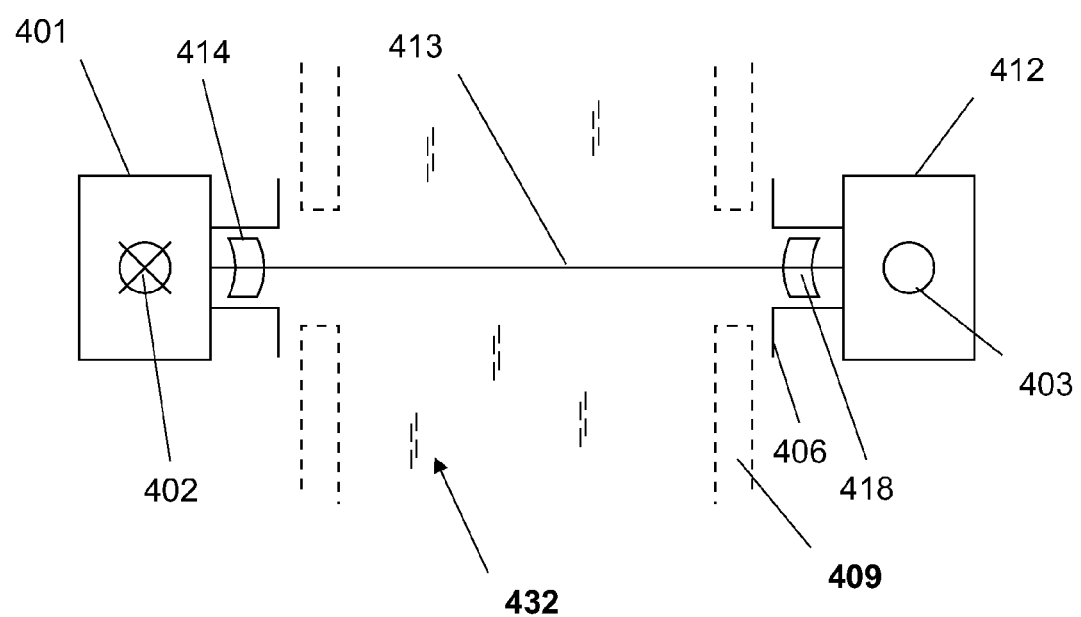
FIG. 4 shows a fourth exemplary embodiment of a gas analyser as disclosed herein with a first and a second process window and a first and a second housing, wherein in the first housing a laser and in the second housing a detector are arranged.

FIG. 4 shows a highly diagrammatic view of a fourth exemplary embodiment of a gas analyser as disclosed herein. As already shown in FIG. 3, the gas analyser can include a laser 402, arranged in a first housing 401, and a detector 403, arranged in a second housing 412. The two housings 401, 412 are arranged opposite each other and can, as diagrammatically indicated, be attached to a container 409, for example an inlet line or an outlet line. It would also be possible to use this arrangement as a so-called open-path arrangement for analysing a measurement environment outside a container. In contrast to the embodiments shown in FIGS. 1 to 3, the fourth embodiment need not include a gas probe. In each housing 401, 412 a process window 414, 418 is arranged that is designed as an afocal meniscus lens, whose convex surface in this embodiment faces the measurement medium 432. In this embodiment the optical beam path 413 passes directly through the measurement environment containing the measurement medium 432 or through the container 409.

FIG. 5 shows a section drawing of a gas analyser as disclosed herein. The gas analyser includes a first housing 501 with a laser and a detector. By means of a flange 506 the first housing 501 is captively attached to a counterflange 508 of a gas probe 507.

The gas probe 507 can include a flange body 530 that is connected to a cylindrical probe body 510. In the flange body 530 an afocal meniscus lens is arranged as a process window 521 in such a manner that its concave surface faces the measurement medium. The process window 521 has been sealingly fitted, by means of a seal 528, namely in the embodiment shown an O-ring, to the flange body 530 so that even without the housing 101 no measurement medium can issue from the container 509 through the gas probe 507.

The probe body 510 can include several process openings 511 so that a gaseous measurement medium can flow through the probe body 510. The flange body 530 can include a further flange 519, by way of which the gas probe 507 is connected to a flange 516 in the wall of a container 509.

The gas probe 507 ends in a neck 531, in which an optical reflector element 512 is suspended, without a seal, in the suspension device 527. In this arrangement the optical reflector element 512 is designed as a triple prism.

Furthermore, on the flange body 530 a gas inlet 520 for a purge gas is arranged. By way of a purge-gas line 523 that extends parallel to the longitudinal axis of the probe body the purge gas can be distributed in the probe body 510 in such a manner that during operation at least in the region 529 upstream of the process window 514 a purge-gas cushion can form. Likewise, purge gas can flow around the optical reflector element 512 so that the regions 524 and 525 also can include a purge-gas cushion during operation. To this effect the purge gas is conveyed from the gas connection by way of the purge-gas line 523 through the probe body 510 and exits through the openings 521, 522 and 526 at various locations in the probe body 510 from the purge-gas line 523. The opening 521 is located in the flange body, the openings 522 between the flange body 530 and the neck 531, and the openings 526 are near the optical reflector element 512. The embodiment of the gas probe with a purge-gas connection and a purge-gas line, which embodiment is shown in FIG. 5, can of course also be implemented in the gas analysers with a gas probe as shown above.

Although the disclosure has been described with reference to the specific exemplary embodiments shown, it will be apparent that numerous further embodiment variants can be created with the knowledge of the present disclosure, for example, in that the characteristics of the individual exemplary embodiments are combined, and/or individual functional units of the exemplary embodiments are exchanged. The arrangements shown as examples in the figures can be implemented with different reflector elements as well as with or without gas probes.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

LIST OF REFERENCE CHARACTERS 101, 201, 301, 401, 501 First housing
102, 202, 302, 402 Laser
103, 203, 303, 403 Detector
104 Control and/or regulation unit
105 Connection
106, 206, 306, 506 Flange
107, 207, 307, 507 Gas probe
108, 208, 308, 508 Flange
109, 209, 309, 409, 509 Container/container wall 110, 210, 310, 510 Probe body
111, 211, 311, 511 Process opening
112, 212, 512 Optical reflector element
113, 213, 313, 413, 513 Optical beam path
114, 214, 314, 414, 514 First process window
215 Lead-through
216 Flange
217, 317, 417 Second housing
218, 318, 418 Second process window
519 Flange
520 Gas connection
521 Opening
522 Opening
523 Purge-gas line
524 Region
525 Region
526 Opening
527 Mount
528 Seal
529 Region
530 Flange body
531 Neck
432 Measurement medium

What is claimed is:

1. A gas analyser for absorption-spectroscopic in-situ determination of at least one chemical and/or physical parameter of a gaseous measurement medium, wherein the gas analyser comprises:
a first housing;
at least one laser as a radiation source, which laser is arranged in the first housing;
at least one first process window for coupling radiation emitted by the laser into a measurement medium; and
at least one detector configured to detect radiation following interaction with the measurement medium wherein the first process window is configured as an afocal meniscus lens having a body, the body having a convex surface and a concave surface opposite the convex surface.

2. The gas analyser according to claim 1, comprising:
an optical reflector element that reflects radiation coupled into the measurement medium back to the first process window.

3. The gas analyser according to claim 2, wherein the optical reflector element comprises:
at least one component of cat's eyes optics, at least one triple prism, at least one triple mirror, or at least one planar mirror or imaging mirror.

4. The gas analyser according to claim 3, wherein the chemical and/or physical parameter to be determined comprise/comprises:
at least one of the following parameters: temperature, pressure and/or a concentration of at least one gas selected from a group consisting of oxygen, carbon dioxide, carbon monoxide, nitrogen oxides, ammonia, amines, hydrogen halides, hydrogen sulphides, sulphur dioxide, water and mixtures thereof.

5. The gas analyser according to claim 2, wherein the detector and the laser are arranged in the first housing, and the first process window is arranged for coupling radiation when emitted by the laser to a measurement medium and, following interaction with the measurement medium, also for coupling radiation from the measurement medium.

6. The gas analyser according to claim 5, comprising:
a gas probe having an essentially cylindrical probe body with at least one process opening through which, during operation, a measurement medium can enter into an interior of the probe body, wherein during operation one end of the gas probe is connected to the first housing.

7. The gas analyser according to claim 2, comprising:
a second housing; and
a second process window, wherein the detector or the optical reflector element is arranged in the second housing; and
a gas probe having an essentially cylindrical probe body with at least one process opening through which, during operation, a measurement medium can enter into an interior of the probe body, wherein during operation one end of the gas probe is connected to the first housing.

8. The gas analyser according to claim 1, wherein the detector and the laser are arranged in the first housing, and the first process window is arranged for coupling radiation when emitted by the laser to a measurement medium and, following interaction with the measurement medium, also for coupling a radiation from the measurement medium.

9. The gas analyser according to claim 1, comprising:
a second housing; and
a second process window, wherein the detector is arranged in the second housing.

10. The gas analyser according to claim 9, wherein the second process window is configured as an afocal meniscus lens that comprises:
a body having a convex surface and a concave surface opposite the convex surface.

11. The gas analyser according to claim 1, comprising:
a gas probe having an essentially cylindrical probe body with at least one process opening through which, during operation, a measurement medium can enter into an interior of the probe body, wherein during operation one end of the gas probe is connected to the first housing.

12. The gas analyser according to claim 11, wherein the gas probe comprises:
a purge-gas connection for a purge gas; and
at least one purge-gas line.

13. The gas analyser according to claim 12, configured such that during operation the first process window and/or the second process windows/window will comprise:
a purge-gas cushion on a side of a measurement medium.

14. The gas analyser according to claim 1, wherein the first process window is a non-coated process window or has no anti-reflection coating.

15. A gas analyser for absorption-spectroscopic in-situ determination of at least one chemical and/or physical parameter of a gaseous measurement medium, wherein the gas analyser comprises:
a first housing;
at least one laser as a radiation source, which laser is arranged in the first housing;
at least one first process window for coupling radiation emitted by the laser into a measurement medium; and
at least one detector configured to detect radiation following interaction with the measurement medium wherein the first process window is configured as an afocal meniscus lens having a convex surface and a concave surface;
an optical reflector element that reflects radiation coupled into the measurement medium back to the first process window; and
wherein the optical reflector element is attached without a seal, and arranged such that, during operation, purge gas will flow around the reflector element.

16. The gas analyser according to claim 15, wherein the laser is a tunable laser.

17. The gas analyser according to claim 15, wherein the chemical and/or physical parameter to be determined comprise/comprises:
   at least one of the following parameters: temperature, pressure and/or a concentration of at least one gas selected from a group consisting of oxygen, carbon dioxide, carbon monoxide, nitrogen oxides, ammonia, amines, hydrogen halides, hydrogen sulphides, sulphur dioxide, water and mixtures thereof.

18. The gas analyser according to claim 15, comprising:
   a second housing; and
   a second process window, wherein the detector or the optical reflector element is arranged in the second housing.

19. The gas analyser according to claim 15, comprising:
   a gas probe having a generally cylindrical probe body with at least one process opening through which, during operation, a measurement medium can enter into an interior of the probe body, wherein during operation one end of the gas probe is connected to the first housing.

20. A gas analyser for absorption-spectroscopic in-situ determination of at least one chemical and/or physical parameter of a gaseous measurement medium, wherein the gas analyser comprises:
   a first housing;
   at least one laser as a radiation source, which laser is arranged in the first housing;
   at least one first process window for coupling radiation emitted by the laser into a measurement medium; and
   at least one detector configured to detect radiation following interaction with the measurement medium wherein the first process window is configured as an afocal meniscus lens having a convex surface and a concave surface;
   an optical reflector element that reflects radiation coupled into the measurement medium back to the first process window;
   a second housing; and
   a second process window, wherein the detector or the optical reflector element is arranged in the second housing;
   a gas probe having an essentially cylindrical probe body with at least one process opening through which, during operation, a measurement medium can enter into an interior of the probe body, wherein during operation one end of the gas probe is connected to the first housing; and
   wherein the optical reflector element is attached without a seal, and arrange such that, during operation, purge gas will flow around the reflector element.

* * * * *